United States Patent [19]

Tyle

[11] Patent Number: 4,857,506
[45] Date of Patent: Aug. 15, 1989

[54] SUSTAINED RELEASE GROWTH HORMONE COMPOSITIONS FOR PARENTERAL ADMINISTRATION AND THEIR USE

[75] Inventor: Praveen Tyle, Trenton, N.J.

[73] Assignee: American Cyanamid Company, Stamford, Conn.

[21] Appl. No.: 2,536

[22] Filed: Jan. 12, 1987

[51] Int. Cl.$^4$ ..................... A61K 37/02; A61K 37/24; A61K 37/36

[52] U.S. Cl. ......................................... 514/12; 514/2; 514/21; 514/937; 514/938; 514/964; 530/324; 530/399

[58] Field of Search ....................... 514/12, 2, 21, 937, 514/938, 964; 530/324, 399

[56] References Cited

U.S. PATENT DOCUMENTS 4,521,409 6/1985 Bauman ............................... 424/108

OTHER PUBLICATIONS

Elson et al., "Chemotherapeutic Effect of a Water-Oil-Water Emulsion of Methotresate on the Mouse Lizio Leukaemia", *Rev. Europ. Etudes Clin. et. Biol.*, 1970, XV, 87–90.

Moshe et al., "Pharmaceutical Compositions Comprising a Water-In-Oil-In-Water Emulsion", CA 105 (12): 102606f.

Tanabe Seiyaku KK, "Insulin-Containing Water-Oil-Water Emulsions-Comprising a Fatty Acid Oil, A Polyoxyethylene or Phospholipid Emulsifier, Insulin and Water", J55017328-A, Feb./1980, Biosis Abstract.

Asher et al., "Injectable Pharmaceutical Mixture", CA:88(14):94825q, 1977.

*Primary Examiner*—John Kight
*Assistant Examiner*—Nathan M. Nutter
*Attorney, Agent, or Firm*—Alice C. Brennan

[57] ABSTRACT

The invention relates to sustained release compositions of growth hormones and/or related compounds and multiple water-in oil-in-water emulsions. The invention also relates to methods for increasing and maintaining increased levels of growth hormones and/or related compounds in the blood of treated animals for extended periods of time, increasing weight gains in animals and increasing milk production of lactating animals by the administration of a composition of the invention.

14 Claims, No Drawings

SUSTAINED RELEASE GROWTH HORMONE COMPOSITIONS FOR PARENTERAL ADMINISTRATION AND THEIR USE

BACKGROUND OF THE INVENTION

Advances in the fields of biotechnology and genetic engineering have resulted in the availability of sufficient quantities of biologically active macromolecules such as growth hormones and/or related compounds to make the administration of these agents on a commercial scale economically feasible. Administration of growth hormones and/or related compounds to animals has been reported to provide beneficial effects such as increasing weight gains, increasing milk production in lactating animals, increasing growth rate, increasing feed efficiency, increasing muscle size, decreasing body fat and improving the lean meat to fat ratio.

The above beneficial effects may be accomplished by daily injection or periodic injection of sustained release or prolonged release compositions. Pending Application for United States Letters Patent by S. Cady, R. Fishbein, U. Schroder, H. Erickson, and B. Probasco, Ser. No. 830,158, filed Mar. 20, 1986, and Application for United States Letters Patent of W. Steber, R. Fishbein and S. Cady, Ser. No. 895,608, filed Aug. 11, 1986 and now abandoned, described sustained release compositions utilizing water dispersible carbohydrate polymer-aqueous systems and solid fat and/or wax-oil systems respectively. Prolonged release nonaqueous compositions of polypeptides, preferably associated with metals or metal compounds, and which may additionally contain antihydration agents dispersed in biocompatible oils, are described in European Patent Application No. 85870135.2, published Apr. 4, 1986.

Multiple water-in oil-in water emulsions, represented as W/O/W emulsions, are described as suitable vehicles for the administration of chemotherapeutic agents by L. A. Elson, et al., in *Rev. Europ. Etudes Clin. Et Biol.*, 1970, XV, 87–90 and by J. Benoy et al., in *Proceedings of the British Pharmacological Society*, Mar. 28 and 29, 1972, 135–136. The use of multiple W/O/W emulsions for oral administration of insulin has been reported by M. Schichiri et al., in *Diabetes*, Vol. 24, No. 11, 971–976 (1975), and Diabetologia, 10,317–321 (1974).

U.S. Pat. No. 4,083,798 describes pourable multiple W/O/W emulsion compositions which are stabilized by the presence of 1% to 4% on a weight basis of a water soluble protein and 1 to 4% on a weight basis of a gelling polysaccharide in the external aqueous phase. S. Matsumoto et al., *Journal of Colloid and Interface Science*, Vol. 77, No. 2, 555–563 (1980), describe the effects of osmotic pressure gradients on the water permeability of oil layers in W/O/W multiple emulsions; and A. Abd-Elbary, et al., *Pharm. Ind.*, No. 9, 964–969 (1984) describe the efficacy of different emulsifying agents for preparing multiple emulsions.

It is an object of this invention to provide injectable sustained release compositions of a growth hormone and/or a related compound, wherein the internal aqueous phase contains the growth hormone and/or related compound emulsified in an oil phase which in turn is emulsified in an aqueous phase.

SUMMARY OF THE INVENTION

The present invention is directed to novel sustained release multiple water-in oil-in water ($W_1/O/W_2$) emulsions comprising an internal aqueous phase ($W_1$) containing a growth hormone, growth factor, somatomedin, or biologically active fragment or derivative thereof: dispersed in a water immisciable liquid or oil phase (O); dispersed in an external aqueous phase ($W_2$). The invention is also directed to methods for elevating and maintaining elevated blood levels of a biologically active growth hormone, growth factor somatomedin, or a biologically active fragment or derivative thereof for the purpose of increasing weight gains, growth rate, milk production, or muscle size, improving feed efficiency, and/or decreasing body fat and improving lean meat to fat ratio in an animal.

DETAILED DESCRIPTION OF THE PREFERRED EMBODIMENTS

The compositions of the invention comprise on a weight basis an internal aqueous phase ($W_1$) of about 55% to 99.7% water, 0.2% to 5% salts and/or buffers, 0.1% to 40% of growth hormone, growth factor, somatomedin or a biologically active fragment or derivatives thereof, 0% to 40% polyol, glycol or sugar, and 0% to 2% preservatives and/or stabilizers, dispersed in an oil phase (O) of about 65% to 98% pharmaceutically and pharmacologically acceptable oil or water immiscible liquid, 2% to 40% non-ionic surfactant(s), 0% to 15% thickening agent, gelling agent or a mixture thereof, dispersed in a second aqueous phase ($W_2$) of about 38% to 98% water, 0.2% to 5% salts and/or buffers, 2% to 20% non-ionic surfactant(s), 0% to 15% thickening agent, gelling agent, or a mixture thereof, 0% to 2% perservatives and/or stabilizer, 0% to 60% polyol, glycol or a sugar. Preferred compositions of the invention comprise a $W_1/O/W_2$ emulsion on a weight ratio basis of from 1/1/1 to 1/3/8 of the various phases as described above.

Stabilizers, preservatives, surfactants, glycols, polyols, sugars, thickening agents, gelling agents, salts, buffers and mixtures thereof which are employed in the compositions of the invention normally comprise on a weight basis from 10% to 25% and preferably 14% to 25% of the total composition. These excipients provide maximum stability of the multiple emulsion, adjust the viscosity of the final composition and control the rate of release of the biologically active agent from the inner aqueous phase by providing the appropriate concentration gradient between the inner aqueous phase ($W_1$) and the outer aqueous phase ($W_2$).

Preferred salts and buffers employed in the aqueous phases of the invention are those which are normally used in the preparation of phosphate buffered saline (PBS), containing $NaH_2PO_4 \cdot H_2O$ (0.025 mol), $Na_2HPO_4$ (0.025 mol), and NaCl (0.15 mol), adjusted to pH 7.1; carbonate buffered saline (CBS), containing $Na_2CO_3$ (0.025 mol), $HaHCO_3$ (0.025 mol), and NaCl (0.15 mol), adjusted to pH 9.4; and saline.

Preferred stabilizers employed in the compositions of the invention include dehydroacetic acid and salts thereof, preferably the sodium salt; salicylanilide; sorbic acid, boric acid, benzoic acid and salts thereof; sodium nitrite and sodium nitrate.

Preferred non-ionic surfactants for use in the compositions of the invention include the sorbitan oleates and stearates, polyethoxylated sorbitan oleates, and block copolymers of ethylene oxide and propylene oxide; with total amounts of from 2% to 20% on a weight basis being distributed between the oil phase (O) and the outer aqueous phase being preferred.

A preferred embodiment of this invention is the incorporating of 1% to 10% of sorbitan monooleate, sorbitan trioleate, sorbitan sesquioleate, ethoxylated (5) soya sterol or sorbitan monostearate in the oil phase (O); in conjunction with the incorporation of 1.0% to 10% of polyoxyethylene (20) sorbitan monooleate or a block copolymer of ethylene oxide and propylene oxide in the outer aqueous phase ($W_2$).

Thickening agents, gelling agents and sugars useful in the compositions of the invention may be naturally occurring or synthetic in origin. Thickening agents, gelling agents, suspending agents, bulking substances, tonicity modifiers, or sugars with aluminum monostearate, aluminum distearate, aluminum tristearate, gelatin, polyvinyl pyrrolidone, sodium alginate, sodium carboxymethyl cellulose, methyl cellulose, polyethylene glycol, sorbitol, mannitol, glycerol, and lactose are preferred.

Pharmaceutically and pharmacologically acceptable water immiscible liquids suitable for use as the oil phase of the invention include oils, liquid fats, water immiscible alcohols and glycols or mixtures thereof.

Preferred water immisciable liquids for use as the oil phase (O) in the compositions of the invention include fatty acid glycerides and blends thereof which are liquid at ambient temperatures. Representative examples are synthetic oils, light mineral oils, heavy mineral oils, vegetable oils, such as olive, sesame seed, peanut, sunflower seed, soybean, cottonseed, corn, safflower, palm, rapeseed and coconut; animal oils such as fish oils, fish liver oils, sperm oils; or fractions derived therefrom; and mixtures thereof.

Biologically active agents suitable for administration in the compositions of the invention include growth hormones, somatomedins, growth factors, and other biological active fragments and derivatives thereof. Preferred agents include bovine, ovine, equine, porcine, avian, and human growth hormones. The term growth hormones encompasses those which are of natural, synthetic, recombinant or biosynthetic origin.

The invention is further illustrated by the following non-limiting examples.

EXAMPLE 1

Preparation of sustained release growth hormone multiple emulsions compositions

Procedures

A. Emulsification by Syringe Technique

Lyophilized recombinant bovine growth hormone is dissolved in the primary aqueous phase ($W_1$) and then taken up in a 10 mL all glass syringe. The oil phase is taken up into a second syringe. All air is expelled from both syringes and they are connected via a three way stopcock with Luer-Lok fittings (Pharmaseal K75). The two phases are mixed by passing them from one syringe to another for a specific number of exchanges. All of the sample ($W_1$/O primary emulsion) is then pushed into one syringe and the secondary aqueous phase ($W_2$) taken up into the second syringe. Multiple emulsification ($W_1$/O/$W_2$) is then accomplished by once again passing the contents of the syringe back and forth. Sufficient multiple emulsion is prepared to provide dosage for testing. The emulsions are remixed prior to each injection to insure that a homogeneous dispersion of the primary emulsion is being administered.

B. Emulsification by Homogenization

Lyophilized recombinant bovine growth hormone is dissolved in the primary aqueous phase ($W_1$) in a beaker and oil phases added to the beaker with continuous homogenization by a Tissumizer (Tekmar, model SDT-1810) at low speed (20–40 V). The $W_1$/O primary emulsion formed is then added with homogenization to the beaker containing the external aqueous phase ($W_2$). The multiple emulsion formed is checked by brightfield light microscopy.

Utilizing the above procedures with the materials listed in Table I below yields the multiple ($W_1$/O/$W_2$) emulsion growth hormone compositions listed in Table II below.

TABLE I

| Abbreviation | Material |
| --- | --- |
| K. Alg | Potassium Alginate |
| HVO | Hydrogenated Vegetable Oil |
| LMO | Light Mineral Oil |
| HMO | Heavy Mineral Oil |
| CBS | Carbonate Buffered Saline |
| CB | Carbonate Buffer |
| Gel | Gelatin Type A, 150 Bloom |
| Corn | Corn Oil |
| Cot | Cotton Seed Oil |
| Ses | Sesame Oil |
| Lect | Lecithin UF—H |
| AMS | Aluminum Monostearate |
| Dextrin | Carbohydrate (Nadex 772) |
| BW | Beeswax |
| Sq | Squalene |
| CO | Castor Oil (Trylox-CO5, Emery) |
| CMC | Carboxymethyl cellulose |
| PG | Propylene Glycol |
| STO | Sorbitan trioleate |
| SMO | Sorbitan monooleate |
| SSO | Sorbitan Sesquioleate |
| MMO | Mannide monooleate |
| PSMS | Polyoxyethylene (20) sorbitan monostearate |
| PSMO | Polyoxyethylene (20) sorbitan monooleate |
| SMS | Sorbitan monosteatate |
| PSML | Polyoxyethylene (20) sorbitan monolaurate |
| PSE | Polyoxyethylene (2) stearyl ether |
| POE | Polyoxyethylene (2) oleyl ether |
| SLI | Sodium lauriminodipropionate |
| $BCP_1$ | Block copolymer of ethylene-oxide and propylene oxide Average molecular weight - 8,350 |
| $BCP_2$ | Block copolymer of ethylene-oxide and propylene oxide Average molecular weight - 5,000 |
| $BCP_3$ | Block copolymer of ethylene-oxide and propylene oxide Average molecular weight - 7,700 |
| $BCP_4$ | Block copolymer of ethylene-oxide and propylene oxide Average molecular weight - 10,800 |
| $BCP_5$ | Block copolymer of ethylene-oxide and propylene oxide Average molecular weight - 12,500 |
| Sorb | Sorbitol aqueous solution USP (70% w/w) |
| EPS | Ethoxylated (5) Phytosterol |

TABLE II

| Composition | Phase $W_1$ containing growth hormone Components (% w/w) | Phase O Components (% w/w) | Phase $W_2$ Components (% w/w) | $W_1/O/W_2$ ratio |
|---|---|---|---|---|
| 1 | CBS(100) | LMO(90),STO(10) | CBS(93), Sorb(5),PSMO(2) | 1/1/1.33 |
| 2 | CBS(100) | HMO(96),SMO(10),AMS(2),PSMO(2) | CBS(93),PSMO(2),Sorb(5) | 1/1/1.33 |
| 3 | CBS(100) | HMO(92.3),SMS(7.7) | CBS(97),$BCP_1$(3) | 1/1/1.33 |
| 4 | CBS(100) | HMO(89),EPS(11) | CBS(97),$BCP_1$(3) | 1/1/1.33 |
| 5 | CBS(100) | HMO(90),MMO(10) | CBS(93),PSMO(2),Sorb(5) | 1/1/2 |
| 6 | CBS(100) | HMO(82),Lect.(13),PSMO(5) | CBS(91),SMO(2),PSMO(7) | 1/1/2 |
| 7 | CBS(100) | LMO(88),AMS(1),MNO(10),PSMO(1) | CBS(97.8),Gel(0.2),PSMO(2) | 1/1/1 |
| 8 | CBS(100) | LMO(76),AMS(2),MMO(20),PSMO(2) | CBS(97),$BCP_1$(3) | 1/1/2 |
| 9 | CBS(100) | LMO(89),AMS(1),STO(10) | CBS(93),Sorb(5),PSMO(2) | 1/1/2 |
| 10 | K.Alg(0.36),Sorb.(5),PSMO(2),CBS Dextrin(3),CBS(90) | HVO(67),MMO(33), | CBS(93),Sorb(5),PSMO(2) | 1/1/1 |
| 11 | CBS(100) | HMO(87.2),SSO(10.5),PSMS(2.3) | CBS(96),Gel(2),PSMO(2) | 1/3/2 |
| 12 | CBS(100) | LMO(89),AMS(10),STO(1) | CBS(96),Gel(2),PSMO(2) | 1/3/8 |
| 13 | CBS(100) | LMO(89),AMS(1),STO(10) | CBS(93),Sorb(5),PSMO(2) | 1/1/1.33 |
| 14 | CBS(100) | LMO(89),AMS(1),STO(10) | CBS(93).Sorb(5),PSMO(2) | 1/1/1.33 |
| 15 | CBS(73),Sorb(25),$BCP_1$(2) | $BCP_2$(12.5),Sq(50),BW(37.5) | CBS(18.75),Sorb(67.5),PSMO(13.75) | 1/1/2 |
| 16 | CBS(67),Sorb(33) | Corn(83.4),CO(16.6) | CBS(95.15),CMC(2),PSMO(1),PSML(1),NaCl(0/85) | 1/2/2 |
| 17 | CBS(67),Sorb(33) | Cot(83.75),PSE(11.25),POE(5) | CBS(83.3)CO(16.6) | 1/2/2 |
| 18 | CBS (100), | Ses(95),SMO(5), | CBS(90),$BCP_3$(5),$BCP_4$(5) | 1.5/2.5 |

EXAMPLE 2

Effectiveness of injectable compositions of the invention

The efficacy of injectable compositions of this invention is demonstrated utilizing a hypophysectomized (hypox) rat assay. The hypophysectomized rat does not produce its own growth hormone and is sensitive to injected bovine growth hormone. The response measured is growth over a period of time such as ten days.

Each of the hypox albino rats (Taconic Farms, Sprague Dawley derived) is injected with a sufficient quantity of representative compositions prepared in Example 1 to provide a dose of 2400 micrograms of bovine growth hormone in 0.2 mL of $W_1/O/W_1$ multiple emulsion.

Test Procedure

Prior to the test, the animlas are weighed and the animals to be used for the test are selected based on body weight. Only those animals whose body weights are one standard deviation from the mean body weight of the group are selected. The resulting group is then randomly divided into treatment groups consisting of eight rats/group by a computer generated randomization procedure. The test animals are then transferred to a clean cage and housed four rats/cage. On the initial day of the study the test animals are weighed and any animals with excessive weight gain or loss (±grams) are replaced. The animals are then assigned to test groups and treated.

At the end of the ten-day test period, total weight gain for each animal is recorded and the average weight gain per rat for each treatment determined. The results of these experiments, which are summarized in Table III below, demonstrate the effectiveness of injectable compositions of this invention.

TABLE III

Efficacy of sustained release compositions of the invention for increasing weight gains in hypox rats

| Composition | Average body weight (g)/animal | | | | | Average weight gain (g)/animal | | | | |
|---|---|---|---|---|---|---|---|---|---|---|
| | Day 0 | Day 2 | Day 4 | Day 7 | Day 10 | Days 0-2 | Days 2-4 | Days 4-7 | Days 7-10 | Days 0-10 |
| 1 | 90.3 | 93.4 | 98.9 | 103.4 | 105.6 | 3.1 | 5.4 | 4.6 | 2.1 | 15.2 |
| 2 | 90.0 | 94.4 | 98.1 | 100.3 | 102.6 | 4.4 | 3.8 | 2.1 | 2.4 | 12.7 |
| 3 | 84.8 | 89.5 | 92.0 | 92.5 | 93.0 | 4.8 | 2.5 | 0.5 | 0.5 | 6.3 |
| 4 | 86.4 | 89.6 | 93.4 | 97.4 | 95.5 | 3.3 | 3.8 | 4.0 | −1.9 | 9.1 |
| 5 | 90.8 | 93.0 | 96.8 | 96.1 | 98.1 | 2.3 | 3.8 | −0.6 | 2.0 | 7.5 |
| 6 | 86.0 | 94.1 | 95.4 | 95.4 | 97.4 | 6.1 | 1.3 | 0.0 | 2.0 | 9.4 |
| 7 | 93.8 | 104.7 | 105.5 | 108.3 | 110.0 | 10.8 | 0.8 | 2.8 | 1.7 | 16.1 |
| 8 | 86.9 | 91.7 | 91.7 | 93.1 | 95.1 | 4.9 | 0.0 | 1.4 | 2.0 | 7.3 |
| 9 | 89.3 | 92.1 | 94.8 | 99.6 | 102.6 | 2.9 | 2.6 | 4.9 | 3.0 | 13.4 |
| 10 | 92.9 | 95.9 | 99.3 | 100.1 | 101.6 | 3.0 | 3.4 | 0.9 | 1.5 | 9.8 |
| 11 | 94.3 | 103.1 | 102.3 | 100.8 | 100.4 | 8.9 | −0.9 | −1.5 | −0.4 | 6.1 |
| 12 | 91.1 | 94.0 | 94.6 | 98.4 | 99.1 | 2.9 | 0.6 | 3.8 | 0.8 | 8.1 |
| 13 | 94.3 | 98.0 | 100.5 | 105.5 | 103.6 | 3.8 | 2.5 | 5.0 | −1.9 | 9.4 |
| 14 | 94.6 | 97.3 | 103.8 | 106.4 | 104.8 | 2.6 | 6.5 | 2.6 | −1.6 | 10.1 |
| 15 | 92.3 | 94.3 | 96.9 | 98.6 | 98.9 | 2.0 | 2.6 | 1.8 | 0.3 | 6.7 |
| 16[1] | 90.9 | 91.0 | 92.7 | 96.4 | 94.9 | 0.1 | 1.7 | 3.7 | −1.6 | 3.9 |
| 17[1] | 89.3 | 89.6 | 92.4 | 92.5 | 92.0 | 0.4 | 2.8 | 0.1 | −0.5 | 2.8 |
| 18 | 91.9 | 97.9 | 97.6 | 102.4 | 104.3 | 6.0 | −0.3 | 4.8 | 1.9 | 12.4 |

[1]Bovine growth hormone dose 1200 micrograms.

EXAMPLE 4

Effectiveness of compositions of the invention for increasing and maintaining increased levels of growth hormone in blood Groups of three wether lambs weighing approximately 35 kg each are treated with the compositions described in Table IV below.

Prior to injecting the formulation, one pretreatment blood sample is obtained from each animal at 24 hours before treatment. These animals are acclimated to the facilities and fed daily at 8:00 a.m. Care is taken so as not to excite the sheep any more than necessary, as this may stimulate a natural release of growth hormone.

On the day of treatment, blood samples are taken just prior to injection. Each sheep then receives a single injection of the formulation. Blood samples are collected at 0, 2, 4, 6, 24, 48, 72, 96 hours and periodically thereafter.

The serum is separated from the clot by centrifugation and the serum frozen and delivered to the Analytical Laboratory for growth hormone by radioimmunoassay procedures.

The results of these experiments which are summarized in Table V below demonstrate the effectiveness of the compositions of the invention for increasing and maintaining increased blood levels of growth hormones. Comparable results are obtained with other compositions of the invention.

TABLE IV

| | Composition | % w/w of Phase | % of Total |
|---|---|---|---|
| A. | $W_1$ Phase | | |
| | Recombinant bovine growth hormone | 12.5 | 3.75 |
| | CBS | 87.5 | 26.3 |
| | O Phase | | |
| | LMO | 89.0 | 27.1 |
| | AMS | 1.0 | 0.03 |
| | STO | 10.0 | 3.0 |
| | $W_2$ Phase | | |
| | CBS | 93.0 | 37.1 |
| | PSMO | 2.0 | 0.8 |
| | Sorb(70%) | 5.0 | 2.0 |
| B. | $W_1$ Phase | | |
| | Recombinant bovine growth hormone | 7.3 | 2.8 |
| | Gel | 13.3 | 5.1 |
| | Water | 79.4 | 30.4 |
| | O Phase | | |
| | SES | 91.9 | 24.9 |
| | CO | 1.8 | 0.5 |
| | SSO | 7.3 | 1.97 |
| | $W_2$ Phase | | |
| | Gel | 1.0 | 0.65 |
| | Water | 79.0 | 26.9 |
| | $BCP_5$ | 20.0 | 6.74 |
| C. | $W_1$ Phase | | |
| | Recombinant bovine growth hormone | 13.25 | 2.65 |
| | CB | 86.75 | 17.35 |
| | O Phase | | |
| | SES | 95.0 | 28.5 |
| | SMO | 5.0 | 1.5 |
| | $W_2$ Phase | | |
| | $BCP_3$ | 5.0 | 2.5 |
| | $BCP_4$ | 5.0 | 2.5 |
| | Water | 90.0 | 45.0 |

TABLE V

Bovine growth hormone blood levels in sheep (ng/mL)

| Time | Sheep # 1 | 2 | 3 | Average |
|---|---|---|---|---|
| Composition A (2 mL) | | | | |
| −24 hrs | 7.1 | 8.0 | 6.6 | — |
| −23 hrs | 5.1 | 4.0 | 4.8 | 4.6 |
| −22 hrs | 5.4 | 4.5 | 3.8 | 4.6 |
| 0 hr | 9.6 | 6.0 | 7.5 | 7.7 |
| 2 hrs | 222.0 | 816.0 | 979.0 | 672.3 |
| 4 hrs | 177.0 | 505.0 | 689.0 | 457.0 |
| 6 hrs | 166.0 | 368.0 | 468.0 | 334.0 |
| 1 day | 146.0 | 49.1 | 77.3 | 90.8 |
| 2 days | 27.9 | 19.8 | 21.5 | 23.1 |
| 3 days | 27.9 | 33.7 | 28.0 | 23.2 |
| 4 days | 21.7 | 11.0 | 22.0 | 11.6 |
| 6 days | 6.6 | 6.6 | 7.4 | 6.9 |
| 8 days | 7.8 | 6.9 | 9.3 | 8.0 |
| 10 days | 10.1 | 7.5 | 7.7 | 8.4 |
| 13 days | 4.7 | 5.3 | 7.1 | 5.7 |
| 15 days | 6.5 | 4.7 | 4.7 | 5.3 |
| 17 days | 5.3 | 3.9 | 8.3 | 5.8 |
| 20 days | 6.4 | 6.6 | 5.8 | 6.3 |
| 22 days | 5.7 | 6.1 | 7.1 | 6.3 |
| 24 days | 2.8 | 4.5 | 6.0 | 4.4 |
| Composition B (5 mL) | | | | |
| −24 hrs | 2.6 | 4.0 | 2.3 | 3.0 |
| 0 hr | 1.5 | 4.0 | 2.9 | 2.8 |
| 1 hr | 13.8 | 10.3 | 10.4 | 11.5 |
| | 11.1 | 8.3 | 8.0 | 9.2 |
| 2 hrs | 376.0 | 66.4 | 38.5 | 160.3 |
| | 20.7 | 24.6 | 20.9 | 22.1 |
| 4 hrs | 109.8 | 102.6 | 53.3 | 88.6 |
| 6 hrs | 171.8 | 119.8 | 156.1 | 149.2 |
| 1 day | 65.1 | 176.4 | 319.4 | 187.0 |
| 2 days | 17.1 | 38.9 | 67.8 | 41.3 |
| 3 days | 9.9 | 22.0 | 31.7 | 21.2 |
| 4 days | 9.6 | 14.6 | 38.9 | 21.0 |
| 5 days | 5.1 | 9.4 | 28.5 | 14.3 |
| 6 days | 2.2 | 7.7 | 48.2 | 19.4 |
| 8 days | 2.0 | 18.3 | 98.1 | 39.5 |
| 10 days | 1.5 | 13.7 | 80.9 | 63.4 |
| 13 days | 1.7 | 11.7 | 81.0 | 31.5 |
| 15 days | 1.8 | 15.1 | 73.7 | 30.2 |
| 17 days | 4.0 | 13.7 | 73.1 | 30.3 |
| Composition C (2.5 mL) | | | | |
| −24 hrs | 2.7 | 2.4 | 1.8 | 2.3 |
| 0 hr | 2.9 | 1.8 | 2.2 | 2.3 |
| 1 hr | 315.5 | 168.0 | 196.3 | 226.6 |
| 2 hrs | 551.2 | 280.6 | 296.9 | 376.2 |
| 4 hrs | 756.8 | 462.2 | 466.7 | 561.9 |
| 6 hrs | 1007.1 | 593.1 | 624.6 | 741.6 |
| 1 day | 70.4 | 91.5 | 142.5 | 101.5 |
| 2 days | 29.0 | 36.0 | 41.1 | 35.4 |
| 3 days | 21.3 | 23.8 | 26.2 | 23.8 |
| 4 days | 15.3 | 11.4 | 18.5 | 15.1 |
| 5 days | 19.2 | 8.3 | 14.3 | 13.9 |
| 6 days | 22.0 | 5.4 | 11.9 | 13.1 |
| 8 days | 21.7 | 8.5 | 8.7 | 12.9 |
| 10 days | 21.6 | 12.3 | 7.2 | 13.7 |
| 13 days | 16.3 | 19.9 | 4.1 | 13.4 |
| 15 days | 17.0 | 19.2 | 3.1 | 13.1 |
| 17 days | 14.5 | 17.5 | 2.2 | 11.4 |
| 20 days | 16.0 | 14.4 | 2.3 | 10.9 |

What is claimed is:

1. A parenteral biologically active sustained release multiple water-in oil-in water, emulsion consisting essentially of an internal aqueous phase $W_1$ containing on a weight basis of about 55.0% to 99.7% water, 0.2% to 5.0% carbonated buffered saline, 0.1% to 40.0% growth hormone, growth factor, somatomedin or a biologically active fragment or derivatives thereof; 0% to 40.0% polyol, glycol or sugar, and 0% to 2.0% preservatives or stabilizers, the oil phase O is comprised on a weight basis of about 65.0% to 98% pharmaceutically and pharmacologically acceptable oil or water immiscible liquid, 0% to 15.0% thickening agent, gelling agent or a mixture thereof, 2.0% to 40.0% non-ionic surfactant(s), the external aqueous phase $W_2$ is comprised on a weight basis of about 38.0% to 98.0% water, 0.2% to 5.0% carbonated buffered saline, 2.0% to 20.0% non-ionic surfactant(s), 0% to 15.0% thickening agent, gelling agent or a mixture thereof, 0% to 2.0% preservative and/or stabilizer and 0% to 60% polyol, glycol, or a sugar.

2. The composition according to claim 1 wherein the ratio of the phases $W_1/O/W_2$ is in the range of from 1/1/1 to 1/3/8 on a weight basis.

3. The composition according to claim 2, wherein the internal aqueous phase contains a bovine, procine, ovine, equine, avian or human growth hormone of natural, synthetic, recombinant or biosynthetic origin.

4. The composition according to claim 3, wherein the surfactants are sorbitan oleates, sorbitan stearates, polyethoxylated sorbitan oleates, block copolymers of ethylene oxide and propylene oxide or mixtures thereof and comprise from about 2% to 20% on a weight basis of the composition.

5. The composition according to claim 4 wherein the oil phase O contains 1% to 10% on a weight basis of sorbitan monooleate, sorbitan trioleate, sorbitan sesquioleate, ethoxylated(5) soya sterol or sorbitan monostearate; and the external aqueous phase $W_2$ contains 1% to 10% on a weight basis of polyoxyethylene(20) sorbitan monooleate or a block copolymer of ethylene oxide and propylene oxide.

6. The composition according to claim 5, wherein the thickening agents, gelling agents or sugars are aluminum monostearate, aluminum distearate, aluminum tristearate, gelatin, polyvinyl pyrrolidone, sodium alginate, sodium carboxymethyl cellulose, methyl cellulose, polyethylene glycol, sorbitol, mannitol, glycerol, or lactose.

7. The composition according to claim 6, wherein the growth hormone is bovine growth hormone.

8. A method for elevating and maintaining elevated blood levels of a biologically active growth hormone, growth factor, somatomedin, or a biologically active fragment thereof for the purpose of increasing weight gains, growth rate, milk production, or muscle size, improving feed efficiency, or decreasing body fat and improving lean meat to fat ratio in an animal comprising parenterally administering to the animal an effective amount of a biologically active sustained release multiple water-in oil-in water emulsion consisting essentially of an internal aqueous phase $W_1$ containing on a weight basis of about 55.0% to 99.7% water, 0.2% to 5.0% carbonated buffered saline, 0.1% to 40.0% growth hormone, growth factor, somatomedin or a biologically active fragment or derivatives thereof; 0% to 40.0% polyol, glycol or sugar, and 0% to 2.0% preservatives or stabilizers, the oil phase O is comprised on a weight basis of about 65.0% to 98% pharmaceutically and pharmacologically acceptable oil or water immiscible liquid, 0% to 15.0% thickening agent, gelling agent or a mixture thereof, 2.0% to 40.0% non-ionic surfactant(s); the external aqueous phase $W_2$ is comprised on a weight basis of about 38.0% to 89.0% water, 0.2% to 5.0% carbonated buffered saline, 2.0% to 20.0% non-ionic surfactant(s), 0% to 15.0% thickening agent, gelling agent or a mixture thereof, 0% to 2.0% preservative and/or stabilizer, and 0% to 60% polyol, glycol, or a sugar.

9. The method according to claim 8, wherein the ratio of the phases $W_1/O/W_2$ is in the range of from 1/1/1 to 1/3/8 on a weight basis.

10. The method according to claim 9, wherein the internal aqueous phase contains a bovine, porcine, ovine, equine, avian or human growth hormone of natural, synthetic, recombinant or biosynthetic origin.

11. The method according to claim 10, wherein the surfactants are sorbitan oleates, sorbitan stearates, polyethoxylated sorbitan oleates, block copolymers of ethylene oxide and propylene oxide or mixtures thereof and comprise from about 2% to 20% on a weight basis of the composition.

12. The method according to claim 11, wherein the oil phase O contains 1% to 10% on a weight basis of sorbitan monooleate, sorbitan trioleate, sorbitan sesquioleate, ethoxylated(5) soya sterol or sorbitan monostearate; and the external aqueous phase $W_2$ contains 1% to 10% on a weight basis of polyoxyethylene(20) sorbitan monooleate or a block copolymer of ethylene oxide and propylene oxide.

13. The method according to claim 12, wherein the thickening agents, gelling agents or sugars are aluminum monostearate, aluminum distearate, aluminum tristearate, gelatin, polyvinyl pyrrolidone, sodium alginate, sodium carboxymethyl cellulose, methyl cellulose, polyethylene glycol, sorbitol, mannitol, glycerol, or lactose.

14. The method according to claim 13, wherein the growth hormone is bovine growth hormone.

* * * * *

UNITED STATES PATENT AND TRADEMARK OFFICE
CERTIFICATE OF CORRECTION

PATENT NO.   : 4,857,506
DATED        : August 15, 1989
INVENTOR(S)  : Praveen Tyle It is certified that error appears in the above-identified patent and that said Letters Patent is hereby corrected as shown below:

In claim 3, Column 9, line 14, "procine" should read --porcine--.

Signed and Sealed this

Twenty-sixth Day of May, 1992

Attest:

DOUGLAS B. COMER

*Attesting Officer*    Acting Commissioner of Patents and Trademarks

UNITED STATES PATENT AND TRADEMARK OFFICE
CERTIFICATE OF CORRECTION

PATENT NO. : 4,857,506

DATED : August 15, 1989

INVENTOR(S) : Praveen Tyle

It is certified that error appears in the above-identified patent and that said Letters Patent is hereby corrected as shown below:

In claim 8, column 10, line 13, "89.0%" should read --98.0%--.

Signed and Sealed this

Twenty-first Day of September, 1993

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 4,857,506

DATED : August 15, 1989

INVENTOR(S) : Pravenn Tyle

It is certified that error appears in the above-identified patent and that said Letters Patent is hereby corrected as shown below:

In claim 8, column 10, line 13, "89.0%" should read --98.0%--.

Signed and Sealed this

Sixteenth Day of November, 1993

Attest:

BRUCE LEHMAN

*Attesting Officer*     Commissioner of Patents and Trademarks